United States Patent [19]

Wirz et al.

[11] Patent Number: 5,087,749
[45] Date of Patent: Feb. 11, 1992

[54] PROCESS FOR THE PREPARATION OF PHENYLSULFONAMIDES

[75] Inventors: Bernard Wirz, Birsfelden; Willy Meyer, Riehen; Wolfgang Stutz, Münchwilen, all of Switzerland

[73] Assignee: Ciba-Geigy Corporation, Ardsley, N.Y.

[21] Appl. No.: 621,406

[22] Filed: Dec. 3, 1990

[30] Foreign Application Priority Data

Dec. 8, 1989 [CH] Switzerland .................. 4413/89

[51] Int. Cl.$^5$ ............................................ C07C 311/15
[52] U.S. Cl. ............................................ 564/90; 564/85; 564/84
[58] Field of Search .................. 564/90, 89, 85, 84

[56] References Cited

U.S. PATENT DOCUMENTS 4,141,916  2/1979  Goralski et al. .......... 564/85
4,476,321  10/1984  Meyer et al. ............. 564/89
4,528,024  7/1985  Lepone ...................... 71/92

FOREIGN PATENT DOCUMENTS 0044808  1/1982  European Pat. Off. .
0074282  3/1983  European Pat. Off. .

OTHER PUBLICATIONS

M. M. Kremlev et all, in: J. of Organ. Chem. USSR, pp. 114–116.
Chemical Abstract 76, 126521h, Kremlev, M. M. et al., (1972) p. 456.

Primary Examiner—Glennon H. Hollrah
Assistant Examiner—Shailendra Kumar
Attorney, Agent, or Firm—Kevin T. Mansfield

[57] ABSTRACT 2-(2-haloethylthio)-phenylsulfonamides of formula I

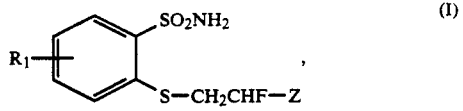

wherein $R_1$ is hydrogen, $C_1$–$C_5$alkyl or $C_2$–$C_5$alkenyl and Z is hydrogen, fluorine or chlorine, are prepared by converting a phenylsulfonamide of formula II

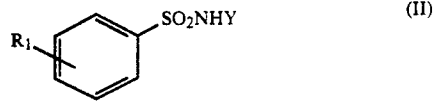

wherein Y is a tertiary alkyl group or a silyl group in succession and without isolating intermediates, with
  a) a strong base MeA, wherein Me is sodium or potassium, A is hydrogen, OH, $NH_2$ or $OR_5$ and $R_5$ is $C_1$–$C_5$alkyl, into the compound of formula III

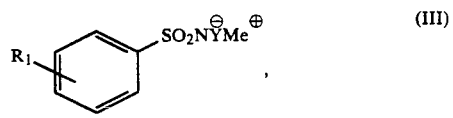

converting that compound with
  b) one equivalent of n-butyllithium and
  c) sulfur
into the compound of formula IV

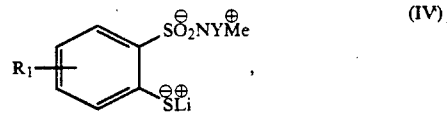

reacting that compound with
  d) a 2-halofluoroethane of the formula X—CH$_2$CH-F—Z wherein X is chlorine or bromine, to form a phenylsulfonamide of formula VI

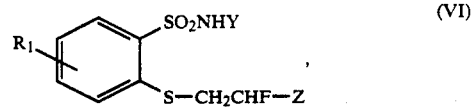

and then removing the group Y.

11 Claims, No Drawings

PROCESS FOR THE PREPARATION OF PHENYLSULFONAMIDES

The present invention relates to a process for the preparation of 2-(2-haloethylthio)-phenylsulfonamides of formula I

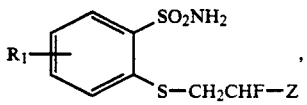
(I)

wherein
$R_1$ is hydrogen, $C_1$–$C_5$alkyl or $C_2$–$C_5$alkenyl; and
Z is hydrogen, fluorine or chlorine.

The 2-(2-haloethylthio)-phenylsulfonamides of formula I are valuable intermediates for the preparation of herbicidally active N-phenylsulfonyl-N'-pyrimidinyl- and -triazinylureas, such as are disclosed, for example, in European Patent Application No. 44808.

Such phenylsulfonylureas derived from the 2-(2-haloethylthio)-phenylsulfonamides of formula I are distinguished by a favourable decomposition behaviour. There is accordingly a need for an advantageous process for the preparation of the 2-(2-haloethylthio)-phenylsulfonamides of formula I.

It is known from EP-A-0074282 to prepare 2-alkylthio-substituted phenylsulfonamides by
1) converting N-tert.-butylphenylsulfonamide with 2 equivalents of n-butyllithium into the dilithium salt of formula VIII

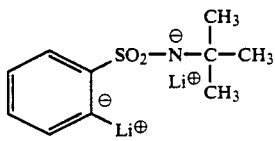
(VIII)

reacting that salt with
2) sulfur and
3) an alkyl halide and then
4) removing the protecting group.

This process has the serious disadvantage, however, that, in order to effect the reaction, 2 equivalents of the expensive n-butyllithium are required per equivalent of the phenylsulfonamide used.

It is accordingly the aim of the present invention to provide a process that permits the preparation of 2-(2-haloethylthio)-phenylsulfonamides in an especially inexpensive and simple manner and with good yields, starting from readily available starting materials.

It has now been found that the 2-(2-haloethylthio)-phenylsulfonamides of formula I can be prepared in advantageous manner when A) a phenylsulfonamide of formula II

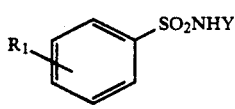
(II)

wherein
$R_1$ is as defined under formula I and

Y is a tertiary alkyl group having from 4 to 8 carbon atoms, benzyl, diphenylmethyl, triphenylmethyl or a silyl group of formula VII $-Si(R_2R_3R_4)$ (VII), wherein each of $R_2$, $R_3$ and $R_4$, independently of the others, is $C_1$–$C_6$alkyl or phenyl, is converted, in succession and without isolating intermediates, with a) a strong base of formula IX MeA (IX), wherein Me is sodium or potassium, A is hydrogen, OH, $NH_2$ or $OR_5$ and $R_5$ is $C_1$–$C_5$alkyl, into the compound of formula III

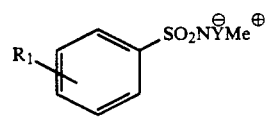
(III)

wherein Me, $R_1$ and Y are as defined above, that compound is converted with b) one equivalent of n-butyllithium and
c) sulfur
into the compound of formula IV

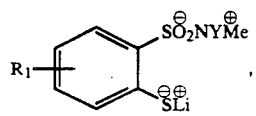
(IV)

wherein Me, $R_1$ and Y are as defined above, that compound is reacted with d) a 2-halofluoroethane of formula V $X-CH_2CHF-Z$ (V)

wherein X is chlorine or bromine and Z is as defined under formula I, to form a phenylsulfonamide of formula VI

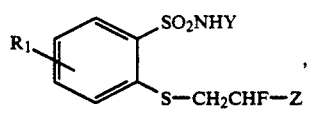
(VI)

wherein Z and $R_1$ are as defined under formula I and Y is as defined under formula II and B) the group Y is then removed.

Starting materials and end products of the process according to the invention are known. Compounds of formulae V and IX are likewise known and are commercially available.

The phenylsulfonamide of formula VI and the salts of formula III are novel and the present invention also includes those compounds.

The alkyl groups occurring in the definitions of the substituents may be straight-chained or branched and are, for example, methyl, ethyl, n-propyl, isopropyl, n-butyl, sec.-butyl, isobutyl, tert.-butyl, n-pentyl or the isomers of pentyl, or n-hexyl or the isomers of hexyl.

The alkyl groups preferably have from 1 to 4 carbon atoms.

The tertiary alkyl groups having from 4 to 8 carbon atoms occurring in the definitions of the substituent Y are, for example, tert.-butyl, 3-methyl-pent-3-yl, 2-methyl-but-2-yl, 3-ethyl-pent-3-yl or 4-methyl-hept-4-yl, but Y is especially preferably tert.-butyl.

The $C_2$–$C_5$alkenyl radicals occurring in the substituent $R_1$ may be straight-chained or branched. Alkenyl radicals having a chain length of two or three carbon atoms are preferred. Examples of $C_2$–$C_5$alkenyl radicals are: vinyl, allyl, methallyl, 1-methylvinyl, 2-methylvinyl, but-2-en-1-yl or pent-3-en-1-yl. Vinyl and allyl are preferred.

Solvents suitable for the reaction according to process step Aa) are open-chained, branched, unbranched or cyclic alkanes and also aromatic compounds. Preferred solvents are toluene, xylene, mesitylene and also alkanes having from 6 to 8 carbon atoms, such as n-hexane, cyclohexane or n-octane. If compounds of formula IX in which A is OH or $OR_5$ are used for process step Aa), it is also possible to use as solvents primary, secondary or tertiary alcohols having from 1 to 5 carbon atoms, such as, for example, methanol, ethanol, isopropanol or butanol. Preferred alcohols are methanol and ethanol.

Preferred strong bases of formula IX are the hydroxides and alcoholates. Sodium hydroxide, potassium hydroxide, sodium methoxide, sodium ethoxide and potassium methoxide are especially preferred.

When Y is a silyl group of formula VII, the reaction is advantageously effected under aprotic conditions. Preferred bases of formula IX are in this case the amides and hydrides; especially preferred bases are sodium amide, sodium hydride and potassium hydride.

Solvents suitable for process steps Ab) to Ad) are, for example, compounds or mixtures from the group of the open-chained and cyclic ethers, such as dioxane, tetrahydrofuran, diethyl ether, diisopropyl ether, dimethoxymethane and 1,2-dimethoxyethane, aromatic hydrocarbons, such as benzene, toluene or xylene, and open-chained alkanes, such as n-pentane or n-hexane. A preferred solvent is tetrahydrofuran.

The reaction of the 2-halofluoroethane of formula V according to process step Ad) can be carried out either at normal pressure or at elevated pressure. A pressure range of from 1 to 10 bar has proved to be very suitable, a range of from 1 to 3 bar being especially preferred.

Solvents suitable for the removal of the group Y according to process step B) are, for example, cyclic and open-chained ethers, such as those mentioned for the process steps Ab) to Ad), and also aliphatic ketones, such as acetone, methyl ethyl ketone, diethyl ketone, methyl isopropyl ketone or methyl isobutyl ketone. Solvents especially well suited to this process step are dioxane and methyl isobutyl ketone.

The group Y is removed in the presence of an acid. The reaction proceeds especially advantageously with trifluoroacetic acid or hydrochloric acid, hydrochloric acid being more especially preferred.

The process according to the invention can be carried out in a wide temperature range. In process step A), the phenylsulfonamide of formula II is advantageously reacted, in succession and without isolating intermediates, with a) a strong base of formula IX at a temperature of from +20° to +250° C., preferably from +60° to +150° C., to form the compound of formula III which b) is converted with n-butyllithium at a temperature of from −80° to +50° C., preferably from −20° to +30° C.; and c) with sulfur at a temperature of from −50° to +50° C., preferably from −10° to +30° C., into the compound of formula IV which is then reacted directly d) with a 2-halofluoroethane of formula V at a temperature of from 0° to +80° C., preferably from +20° to +60° C., and at a pressure of form 1 to 3 bar, to form the compound of formula VI.

A temperature range of from −20° C. to +60° C., preferably from −20° to +30° C., has proved suitable for the removal of the group Y by hydrolysis according to process step B).

Those compounds of formula I in which $R_1$ is hydrogen and Z is at the same time preferably hydrogen can be prepared especially advantageously.

In an especially preferred variant of the process according to the invention, the 2-(2-haloethylthio)-phenylsulfonamide of formula I is prepared by A) converting N-tert.-butylphenylsulfonamide, in succession and without isolating intermediates, with a) sodium methoxide or potassium hydroxide at a temperature of from +60° to +150° C. into the compound of formula IIIa

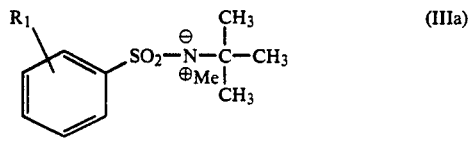

wherein Me is sodium or potassium and $R_1$ is as defined under formula I, converting that compound b) with one equivalent of n-butyllithium at a temperature of from −20° to +30° C. and c) sulfur at a temperature of from −20° to +30° C. into the compound of formula IVa

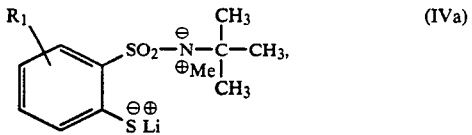

wherein Me is sodium or potassium and $R_1$ is as defined under formula I, reacting that compound with d) a 2-halofluoroethane of formula V at a temperature of from +20° to +60° C. and a pressure of from 1 to 3 bar to form a 2-(2-haloethylthio)-N-tert.-butylphenylsulfonamide of formula VIa

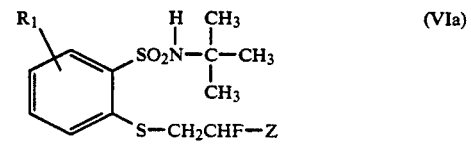

wherein Z and $R_1$ are as defined under formula I, and

B) then removing the tert.-butyl group at a temperature of from −20° to +30° C. in the presence of hydrochloric acid. In this preferred variant of the process according to the invention, Z and $R_1$ are preferably hydrogen.

The process according to the invention is distinguished by numerous advantageous characteristics. The reaction procedure is uncomplicated. The reaction, consisting of only two stages, is especially advantageous from an economic standpoint and requires only little apparatus. The process also gives a high yield and good product quality.

Instead of requiring 2 equivalents of the expensive n-butyllithium per equivalent of phenylsulfonamide used, the process according to the invention requires only one equivalent of n-butyllithium and also sodium or potassium bases which are considerably cheaper.

The process according to the invention is explained in detail by means of the following Examples.

PREPARATION EXAMPLES:

Example 1

Preparation of 2-(2-fluoroethylthio)-N-tert.-butylphenylsulfonamide

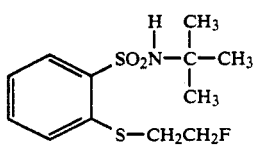

32 g (0.15 mol) of N-(tert.-butyl)-phenylsulfonamide in 120 ml of toluene are added dropwise to a suspension of 9.4 g (0.15 mol) of pulverulent potassium hydroxide (90% strength) in 230 ml of toluene under reflux at a pressure of 0.4 bar using a water separator. The water formed is then removed by azeotropic distillation and the toluene is removed under reduced pressure. The potassium salt of formula III can, if desired, be isolated from the resulting residue for characterisation. The following spectroscopic data were obtained:

| | $^1$H-NMR (300 MHz in DMSO) |
|---|---|
| (structure shown) | 1.10 ppm singlet 9H (tert.-butyl) 7.24 ppm multiplet 3H (arom. meta- and para-protons 7.67 ppm doublet × multiplet 2H Jd = 6 Hz (arom. ortho-protons) |

The residue is made into a slurry with 120 ml of tetrahydrofuran in a nitrogen atmosphere and then cooled to $-15°$ C. 100 ml (0.16 mol) of a 1.6 molar n-butyllithium solution in n-hexane are added dropwise to this suspension within a period of 30 minutes. After stirring for 4 hours at room temperature and cooling again to 0° C., 5.6 g (0.17 mol) of sulfur are added and the reaction mixture is then stirred for a further 3 hours at room temperature. 21.6 g (0.17 mol) of 1-bromo-2-fluoroethane are added to the resulting reaction mixture and the mixture is then stirred for 18 hours at room temperature. The reaction mixture is then diluted with 100 ml of toluene and added to a mixture of 100 ml of ice and 30 ml of concentrated hydrochloric acid. The organic phase is then separated off and concentrated in vacuo until the weight is constant. 43.5 g of 2-(2-fluoroethylthio)-N-tert.-butylphenylsulfonamide (VIa, 83% of the theoretical yield) are obtained in the form of a brown oil having a degree of purity of 83%.

Example 2

Preparation of 2-(2-fluoroethylthio)-phenylsulfonamide

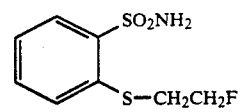

25 ml of trifluoroacetic acid are added at a temperature of 0° C. to a solution of 3.88 g of 2-(2-fluoroethylthio)-N-tert.-butylphenylsulfonamide, obtained in accordance with Example P1, in 25 ml of trichloromethane. After stirring for 18 hours at a temperature of $+25°$ C., the resulting brown reaction mixture is lyophilised. After chromatographic purification of the oily residue with 1) ethyl acetate/petroleum ether (1:1) over silica gel and 2) dichloromethane/acetone (9:1) over silica gel, the resulting fractions are concentrated by evaporation to give 1.5 g (60.5% of the theoretical yield) of crystalline 2-(2-fluoroethylthio)-phenylsulfonamide.

Example 3

Preparation of 2-(2-fluoroethylthio)-phenylsulfonamide

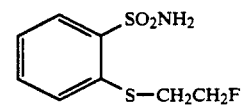

70 ml of concentrated hydrochloric acid are added dropwise at a temperature of from $+20°$ to $+25°$ C., with cooling, to a solution of 18.2 g of 2-(2-fluoroethylthio)-N-tert.-butylphenylsulfonamide (80% strength, 0.05 mol), obtained in accordance with Example P1, in 70 ml of methyl isobutyl ketone. After maintaining the reaction mixture at room temperature for 40 hours, it is neutralised with 30% sodium hydroxide solution and then the aqueous phase is separated off. After removing the solvent under reduced pressure, there are obtained from the organic phase 15.8 g of a crystalline residue which contains the 2-(2-fluoroethylthio)-phenylsulfonamide of formula I in an amount of 70% and in a yield of 94% of the theoretical yield. After recrystallisation from isopropanol, 10.1 g (79% of the theoretical yield) of 2-(2-fluoroethylthio)-phenysulfonamide of formula I are obtained in an amount of 92%.

What is claimed is:

1. A process for the preparation of 2-(2-fluoroethylthio)-phenylsulfonamide of formula I

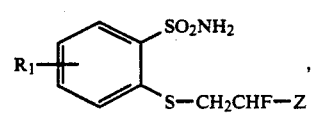

wherein
$R_1$ is hydrogen, $C_1$–$C_5$alkyl or $C_2$–$C_5$alkenyl; and
Z is hydrogen, fluorine or chlorine;
which comprises
A) converting a phenylsulfonamide of formula II

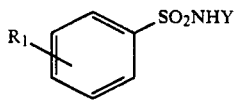

wherein
R₁ is as defined under formula I and
Y is a tertiary alkyl group having from 4 to 8 carbon atoms, benzyl, diphenylmethyl, triphenylmethyl or a silyl group of formula VII

wherein each of R₂, R₃ and R₄, independently of the others, is $C_1-C_6$alkyl or phenyl, in succession and without isolating intermediates, with
a) a strong base of formula IX

wherein Me is sodium or potassium, A is hydrogen, OH, NH₂ or OR₅ and R₅ is $C_1-C_5$alkyl, into the compound of formula III

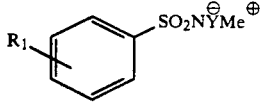

wherein Me, R₁ and Y are as defined above, converting that compound with
b) one equivalent of n-butyllithium and
c) sulfur
into the compound of formula IV

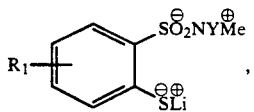

wherein Me, R₁ and Y are as defined above, reacting that compound with
d) a 2-halofluoroethane of formula V

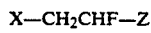

wherein X is chlorine or bromine and Z is as defined under formula I, to form a phenylsulfonamide of formula VI

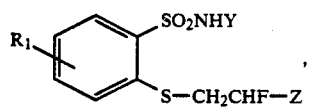

wherein Z and R₁ are as defined under formula I, and Y is as defined under formula II and
B) then removing the group Y.

2. A process according to claim 1, wherein R₁ is hydrogen.

3. A process according to claim 1, wherein Z is hydrogen.

4. A process according to claim 1, wherein A is OH or OR₅.

5. A process according to claim 1, wherein potassium hydroxide or sodium methoxide is used as the strong base of formula IX.

6. A process according to claim 1, wherein X is bromine.

7. A process according to claim 1, wherein Y is tert.-butyl.

8. A process according to claim 1, wherein hydrochloric acid is used for the removal of the group Y.

9. A process according to claim 1, which comprises
A) converting N-tert.-butylphenylsulfonamide, in succession and without isolating intermediates, with
a) sodium methoxide or potassium hydroxide at a temperature of from +60° to 150° C. into the compound of formula IIIa

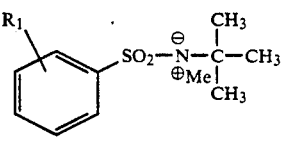

wherein Me is sodium or potassium and R₁ is as defined under formula I in claim 1, converting that compound
b) with one equivalent of n-butyllithium at a temperature of from −20° to +30° C. and
c) sulfur at a temperature of from −20° to +30° C. into the compound of formula IVa

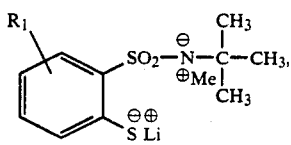

wherein Me is sodium or potassium and R₁ is as defined under formula I in claim 1, reacting that compound with
d) a 2-halofluoroethane of formula V at a temperature of from +20° to +60° C. and a pressure of from 1 to 3 bar
to form a 2-(2-haloethylthio)-N-tert.-butylphenylsulfonamide of formula VIa

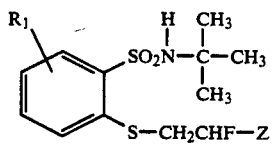

wherein Z and R₁ are as defined under formula I, and
B) then removing the tert.-butyl group at a temperature of from −20° to +30° C. in the presence of hydrochloric acid.

10. A process according to claim 9, wherein R₁ is hydrogen.

11. A process according to claim 9, wherein Z is hydrogen.

* * * * *